United States Patent
Mirza et al.

(10) Patent No.: US 8,679,107 B2
(45) Date of Patent: Mar. 25, 2014

(54) RADIOFREQUENCY PERFORATION APPARATUS

(75) Inventors: Mahmood Mirza, North York (CA); Gareth Davies, Toronto (CA)

(73) Assignee: Baylis Medical Company Inc., Montreal (CA)

(*) Notice: Subject to any disclaimer, the term of this patent is extended or adjusted under 35 U.S.C. 154(b) by 8 days.

(21) Appl. No.: 13/468,939

(22) Filed: May 10, 2012

(65) Prior Publication Data
US 2012/0232546 A1 Sep. 13, 2012

Related U.S. Application Data

(62) Division of application No. 11/905,447, filed on Oct. 1, 2007, now Pat. No. 8,192,425.

(60) Provisional application No. 60/827,452, filed on Sep. 29, 2006, provisional application No. 60/884,285, filed on Jan. 10, 2007.

(51) Int. Cl.
*A61B 18/18* (2006.01)

(52) U.S. Cl.
USPC .................................. 606/33; 606/41

(58) Field of Classification Search
USPC ................. 606/20–52; 607/167, 170
See application file for complete search history.

(56) References Cited

U.S. PATENT DOCUMENTS

| 7,335,197 B2 | 2/2008 | Sage et al. |
| 7,666,203 B2 | 2/2010 | Chanduszko et al. |
| 2006/0264927 A1* | 11/2006 | Ryan ............... 606/45 |

* cited by examiner

*Primary Examiner* — Linda Dvorak
*Assistant Examiner* — Amanda Scott

(57) ABSTRACT

A radiofrequency perforation apparatus for creating a channel at a target location in a body of a patient, the radiofrequency perforation apparatus comprising: a substantially tubular member defining a tubular member lumen; an end member partially positioned within the tubular member lumen at a distal end of the tubular member, the end member including an electrode; and an electrical insulator extending along the substantially tubular member.

21 Claims, 11 Drawing Sheets

RADIOFREQUENCY PERFORATION APPARATUS

CROSS-REFERENCES TO RELATED APPLICATIONS

This application is a divisional application of, and claims priority from, U.S. application Ser. No. 11/905,447, filed on Oct. 1, 2007, and issued Jun. 5, 2012 as U.S. Pat. No. 8,192,425, which claims the benefit of: U.S. provisional application No. 60/827,452, filed on Sep. 29, 2006, and U.S. provisional application No. 60/884,285, filed on Jan. 10, 2007, all of which are incorporated by reference herein in their entirety.

FIELD OF THE INVENTION

The present invention relates generally to methods and devices usable to deliver energy within the body of a patient. More specifically, the present invention is concerned with a radiofrequency perforation apparatus.

SUMMARY OF THE INVENTION

In one broad aspect, embodiments of the present invention comprise a radiofrequency perforation apparatus for creating a channel at a target location in a body of a patient, the radiofrequency perforation apparatus comprising: a substantially tubular member defining a tubular member lumen; an end member partially positioned within the tubular member lumen at a distal end of the tubular member, the end member including an electrode; and an electrical insulator extending along the substantially tubular member.

As a feature of this broad aspect, the electrical insulator includes a first electrically insulating layer at least partially covering the substantially tubular member and a second electrically insulating layer at least partially covering the end member with at least a portion of the electrode electrically exposed, the second electrically insulating layer being thinner than the first electrically insulating layer.

As another feature of this broad aspect, the electrode is substantially atraumatic.

As still another feature of this broad aspect, the electrical insulator extends along at least a portion of the end member with the electrode substantially deprived from the electrical insulator.

As another feature of this broad aspect, the substantially tubular member defines a tubular member outer surface and a tubular member inner surface, the tubular member inner and outer surfaces being distanced from each other by a tubular member thickness, the tubular member thickness being from about 0.05 mm to about 0.4 mm, the tubular member having a maximum outer diameter of from about 0.4 mm to about 1.5 mm.

As still another feature of this broad aspect, the radiofrequency perforation apparatus further comprises a distal tip having a substantially bullet-shaped configuration.

As another a feature of this broad aspect, the electrode is mechanically coupled to the end member.

As an alternative feature of this broad aspect, the electrode is integral with the end member.

As another feature of this broad aspect, the substantially tubular member and the end member are coupled using a method selected from the group consisting of welding, soldering, friction fitting, and using adhesives.

As still another feature of this broad aspect, a total length of the tubular member and the end member at least partially inserted therein is from about 30 cm to about 100 cm.

As another feature of this broad aspect, the substantially tubular member has a length of about 50 cm to about 100 cm and the end member has a length of about 2.5 cm to about 10 cm.

As still another feature of this broad aspect, the substantially tubular member has an outer diameter of about 1.15 mm to about 1.35 mm and the end member has an outer diameter of about 0.40 mm to about 0.80 mm.

As another feature of this broad aspect, the substantially tubular member is made out of stainless steel.

As still another feature of this broad aspect, the end member is made out of a nickel-titanium alloy.

As another feature of this broad aspect, the end member further defines an end member lumen, and a diameter of the tubular member lumen and a diameter of the end member lumen are substantially identical.

As still another feature of this broad aspect, the end member further defines an end member lumen that is in communication with the tubular member lumen and wherein a distal end of the end member is closed.

As another a feature of this broad aspect, the radiofrequency perforation apparatus includes a substantially rectilinear section and a curved section extending from the substantially rectilinear section. As an example of this feature, the curved section has a radius between about 4 cm and about 7 cm and traverses a circumference of a circle between about 50 degrees and about 110 degrees. As another example of this feature, the substantially rectilinear section is made out of a stainless steel and the curved section is made out of nickel-titanium alloy.

As still another feature of this broad aspect, the end member further defines an end member lumen that is in communication with the tubular member lumen, and the end member defines an aperture extending substantially radially outwardly from the end member lumen. As an example of this feature, at least a portion of the tubular member and the end member together define a curved section defining a center of curvature, and the aperture extends from the end member lumen substantially towards the center of curvature. As another example of this feature, the end member defines an end member inner surface, and the end member inner surface is substantially covered with an inner surface electrically insulating material.

The proposed radiofrequency perforation apparatus is relatively easily manufactured using known materials and methods.

In some embodiments of the invention, the proposed radiofrequency perforation apparatus includes a distal tip that may be dragged across tissues adjacent the target site to facilitate the location of the target site. In further embodiments, the distal tip is substantially atraumatic.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
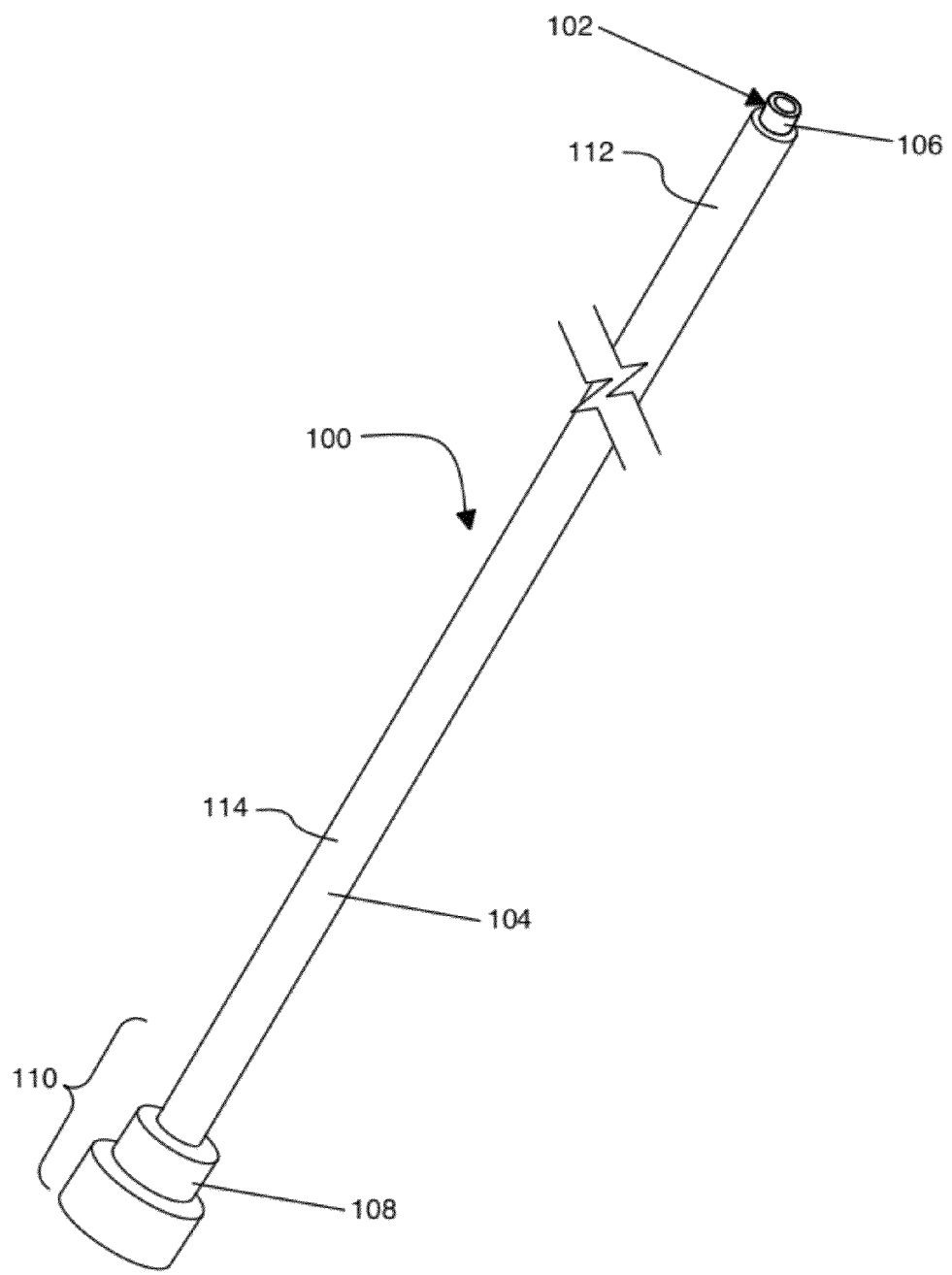
FIG. 1A, in a perspective view, illustrates a radiofrequency perforation apparatus in accordance with an embodiment of the present invention.

With specific reference now to the drawings in detail, it is stressed that the particulars shown are by way of example and for purposes of illustrative discussion of embodiments of the present invention only. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring to FIG. 1A, there is shown a radiofrequency perforation apparatus 100 in accordance with an embodiment of the present invention. The radiofrequency perforation apparatus 100 is usable for creating a channel (not shown in the drawings) at a target location (not shown in the drawings) in a body (not shown in the drawings) of a patient (not shown in the drawings). The radiofrequency perforation apparatus 100 is usable by an intended user (not shown in the drawings) having a hand (not shown in the drawings).

The radiofrequency perforation apparatus 100 includes a handle 110 graspable by the hand (not shown in the drawings), a distal portion 112 and a force transmitting portion 114 extending between the distal portion 112 and the handle 110. The distal portion 112 defines a distal portion length and includes an electrode 106 and an electrical insulator 104 extending from the electrode 106. The force transmitting portion 114 defines a force transmitting portion length, the force transmitting portion length being larger than the distal portion length. In some embodiments of the invention, the force transmitting portion 114 has a force transmitting portion flexural rigidity of at least about $0.016\ Nm^2$, for example about $0.017\ Nm^2$. The force transmitting portion 114 has a force transmitting portion flexural rigidity allowing the transmission to the handle 110 of contact forces exerted on the distal portion 112 when the distal portion 112 contacts the target location to provide tactile feedback to the intended user. In addition, the force transmitting portion flexural rigidity allows for the transmission of force from the handle 110 to the distal portion 112 in order to, for example, advance the distal portion 112 within the body of the patient or to orient the distal portion 112 by applying torque to the handle 110.

Therefore, the proposed radiofrequency perforation apparatus 100 is structured such that it provides the intended user with a similar, or better, 'feel' as some prior art devices. That is, although the structure and function of the radiofrequency perforation apparatus 100 differs significantly from prior art devices.

In some embodiments of the invention, the distal portion 112 has a distal portion flexural rigidity of at least about $0.0019\ Nm^2$, for example $0.0021\ Nm^2$. Once again, if was found that such values optimize the cognitive ergonomics of the proposed radiofrequency perforation apparatus 100 by providing tactile feedback to the intended user and allowing for the transmission of radial (torque) and longitudinal forces from the handle to the distal portion.

In some embodiments of the invention, as illustrated in FIG. 1A the radiofrequency perforation apparatus 100 includes an electrically conductive elongated member 102 having an electrical insulator 104 disposed thereon. The electrical insulator 104 may cover the entire outer surface of the elongated member 102 such that elongated member 102 may deliver energy from its proximal region to the electrode 106 at its distal region, without substantial leakage of energy along the length of the elongated member 102.

As used herein, the terms 'proximal' and 'distal' are defined with respect to the user. That is, the term 'proximal' refers to a part or portion closer to the user, and the term 'distal' refers to a part or portion further away from the user when the device is in use.

Figure 2A:
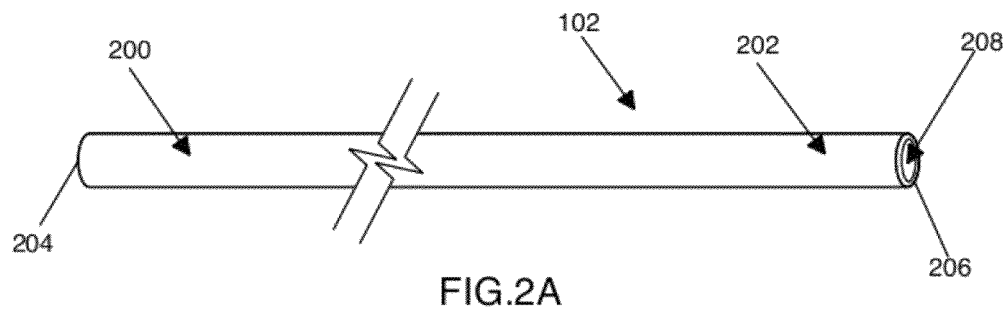
FIG. 2A, in a perspective view, illustrates an elongated member part of the radiofrequency perforation apparatus shown in FIG. 1A.

Referring to FIG. 2A, the elongated member 102 includes a proximal region 200, a distal region 202, a proximal end 204, and a distal end 206. In some embodiments of the invention, the elongated member 102 defines a lumen 208, which may extend substantially between the proximal region 200 and the distal region 202. In some embodiments, one or both of the proximal end 204 and the distal end 206 may be open, thereby defining each at least one aperture 600 (shown, for example, in FIGS. 6A to 6D), which is in fluid communication with the lumen 208.

The elongated member 102 is typically sized such that the handle 110 remains outside of the patient when the distal end 206 is within the body, for example adjacent the target site. For example, the proximal end 204 is at a location outside of the body, while the distal end 206 is located within the heart of the patient. Thus, in some embodiments of the invention, the length of the elongated member 102, i.e. the sum of the force transmitting and distal portion lengths, is between about 30 cm and about 100 cm, depending, for example, on the specific application and/or target site.

The transverse cross-sectional shape of the elongated member 102 may take any suitable configuration, and the invention is not limited in the regard. For example, the transverse cross-sectional shape of the elongated member 102 is substantially circular, ovoid, oblong, or polygonal, among other possibilities. Furthermore, the cross-sectional shape may vary along the length of the elongated member 102. For example, in one embodiment, the cross-sectional shape of the proximal region 200 is substantially circular, while the cross-sectional shape of the distal region 202 is substantially ovoid.

Figure 2B:
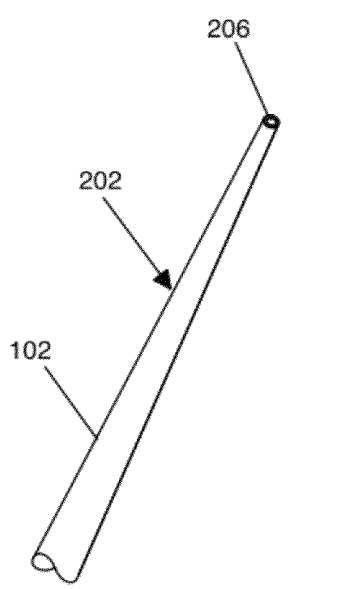
FIG. 2B, in a partial perspective view, illustrates an alternative elongated member usable in the radiofrequency perforation apparatus shown in FIG. 1A.
Figure 2C:
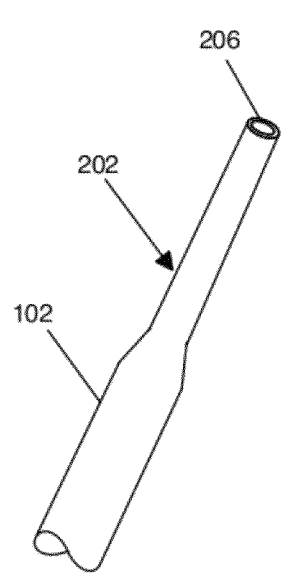
FIG. 2C, in a partial perspective view, illustrates another alternative elongated member usable in the radiofrequency perforation apparatus shown in FIG. 1A.

In outer diameter, the elongated member 102 is sized such that it may fit within vessels of the body of the patient. For example, the outer diameter of the elongated member 102 may be between about 0.40 mm and about 1.5 mm (i.e. between about 27 Gauge and about 17 Gauge). In some embodiments, the outer diameter of the elongated member 102 varies along the length of the elongated member 102. For example, in some embodiments, the outer diameter of the elongated member 102 tapers from the proximal end 204 towards the distal end 206. In one specific embodiment, the outer diameter of the proximal region 200 of the elongated member 102 is about 1.5 mm. In this embodiment, at a point about 4 cm from the distal end 206, the outer diameter may begin to decrease such that the distal end 206 of the elongated member 102 may be about 0.7 mm in outer diameter. In a further embodiment, the outer diameter of the elongated member 102 may taper from about 1.3 mm to about 0.8 mm at a distance of about 1.5 mm from the distal end 206. As shown in FIG. 2B, the taper in elongated member 102 may occur smoothly, for example over a length of about 4 cm or, as shown in FIG. 2C, the taper may occur more abruptly, for example over a length of about 1 mm or less. The taper may be applied to the elongated member 102 by a variety of methods. In some embodiments, the elongated member 102 is manufactured with the taper already incorporated therein. In other embodiments, the elongated member 102 is manufactured without a taper, and the taper is created by swaging the elongate member down to the required outside diameter, or by machining the distal region 202 such that the outside diameter tapers while the inside diameter remains constant.

Figure 2D:
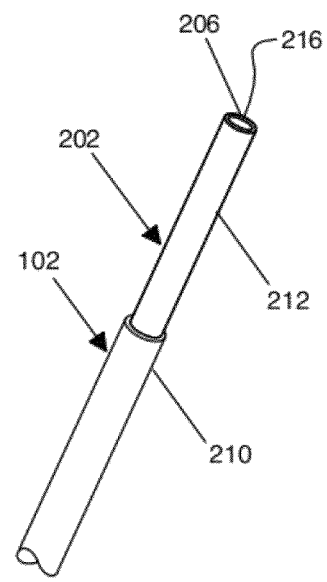
FIG. 2D, in a partial perspective view, illustrates yet another alternative elongated member usable in the radiofrequency perforation apparatus shown in FIG. 1A.
Figure 6A:
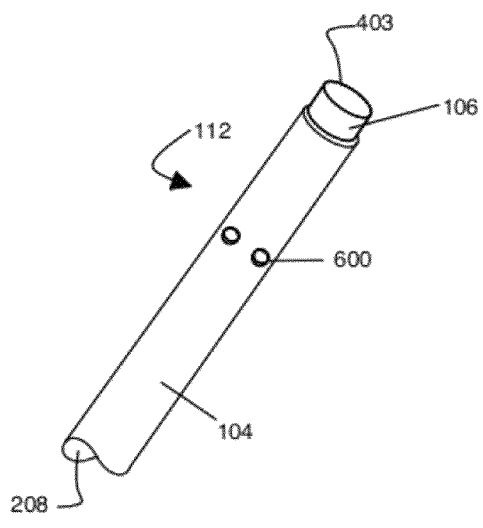
FIGS. 6A to 6E, in partial perspective views, illustrate distal regions that are usable in the radiofrequency perforation apparatuses shown in FIGS. 1A to 3C.
Figure 6B:
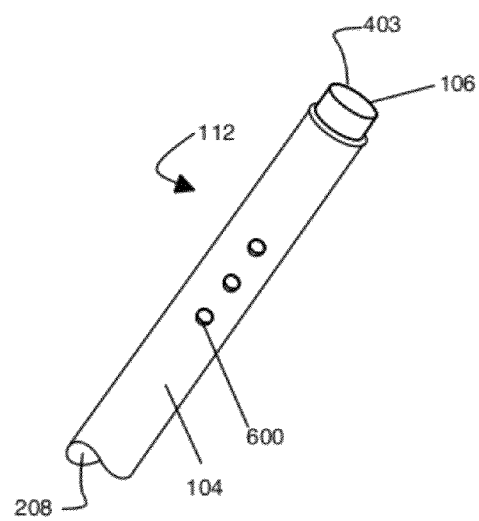
Figure 6C:
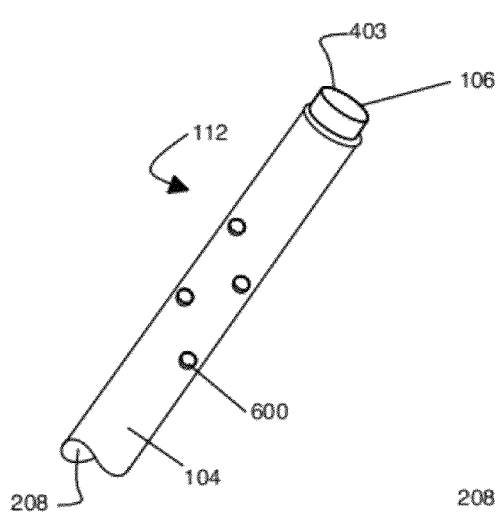
Figure 6D:
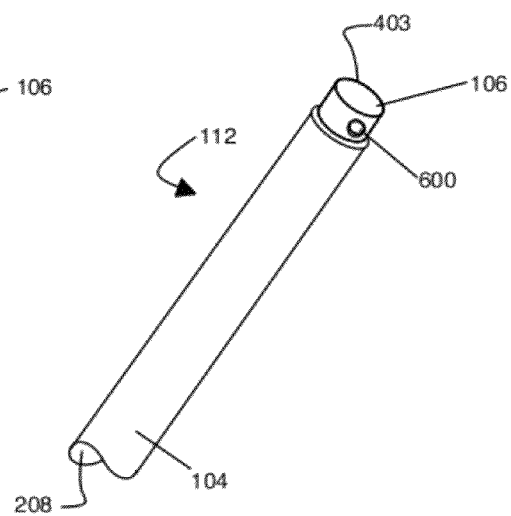
Figure 6E:
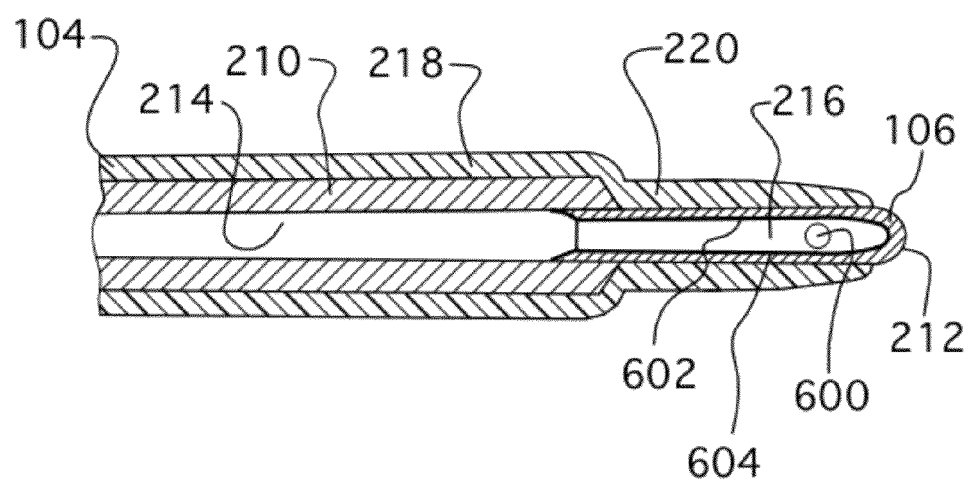

In a further embodiment, the elongated member 102 is manufactured from two pieces of material, each having a different diameter, which are joined together. For example, as shown in FIG. 2D, the elongated member 102 includes a substantially tubular member 210 mechanically coupled to the handle (not shown in FIG. 2D), the substantially tubular member 210 having for example a length of about 50 cm to about 100 cm and an outer diameter of about 1.15 mm to about 1.35 mm. The substantially tubular member 210 defines a tubular member lumen 214, as shown in FIG. 6E, extending substantially longitudinally therethrough. An end member 212, having for example a length of about 2.5 cm to about 10 cm and an outer diameter of about 0.40 mm to about 0.80 mm, is joined to the substantially tubular member 210, such that the substantially tubular member 210 and end member 212 are co-axial. For example, the end member 212 may be inserted partially into the tubular member lumen 214, substantially longitudinally opposed to the handle 110. In some embodiments, the electrode 106 is located about the end member, for example by being mechanically coupled to the end member 212, while in other embodiments the electrode 106 is integral with the end member 212. If the end member 212 defines a lumen 216, as seen in FIGS. 2D and 6E, the lumen 216 is in fluid communication with the tubular member lumen 214, as shown in FIG. 6E. The substantially tubular member 210 and the end member 212 are joined in any suitable manner, for example welding, soldering, friction fitting, or the use of adhesives, among other possibilities. Also, in some embodiments, the tubular member lumen 214 and the lumen 216 have substantially similar diameters, which reduces turbulence in fluids flowing through the tubular member lumen 214 and the lumen 216.

In embodiments of the invention wherein the elongated member 102 defines a lumen 208, the wall thickness of the elongated member 102 may vary depending on the application, and the invention is not limited in this regard. For example, if a stiffer device is desirable, the wall thickness may be greater than if more flexibility is desired. In some embodiments, the wall thickness in the force transmitting region is from about 0.05 mm to about 0.40 mm, and may remain constant along the length of the elongated member 102. In other embodiments wherein the elongated member 102 is tapered, the wall thickness of the elongated member 102 may vary along the elongated member 102. For example, in some embodiments, the wall thickness in the proximal region 200 is from about 0.1 mm to about 0.4 mm, tapering to a thickness of from about 0.05 mm to about 0.20 mm in the distal region 202. The wall may taper from inside to outside, thereby maintaining a consistent outer diameter and having a changing inner diameter. Alternatively, the wall may taper from outside to inside, thereby maintaining a consistent inner diameter and having a changing outer diameter. Furthermore, the wall of the elongated member 102 may taper from both the inside and the outside, for example by having both diameters decrease such that the wall thickness remains constant. For example, in some embodiments, the lumen 208 has a diameter of from about 0.4 mm to about 0.8 mm at the proximal region 200 and tapers to a diameter of from about 0.3 mm to about 0.5 mm at the distal region 202. Alternatively, the outer diameter may decrease while the inner diameter may increase, such that the wall tapers from both the inside and the outside.

Figure 3A:
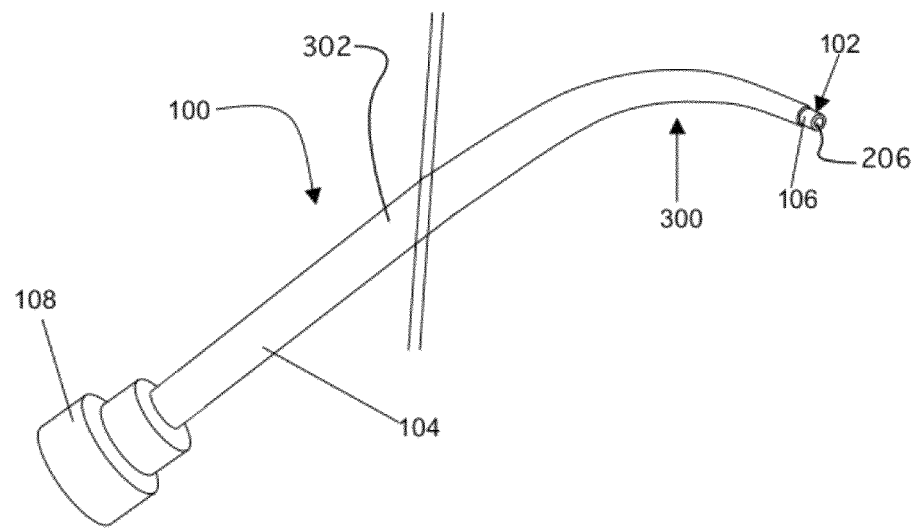
FIG. 3A, in a perspective view, illustrates a radiofrequency perforation apparatus in accordance with an yet another alternative embodiment of the present invention, the radiofrequency perforation apparatus including a curved section.
Figures 3B, 3C:
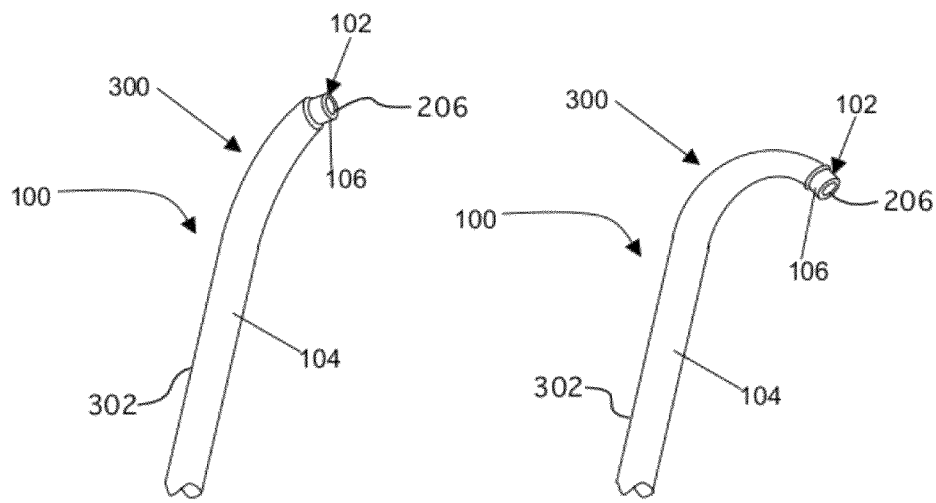
FIG. 3B, in a partial perspective view, illustrates a radiofrequency perforation apparatus in accordance with yet another alternative embodiment of the present invention, the radiofrequency perforation apparatus including an alternative curved section.
FIG. 3C, in a partial perspective view, illustrates a radiofrequency perforation apparatus in accordance with yet another alternative embodiment of the present invention, the radiofrequency perforation apparatus including another alternative curved section.

In some embodiments, the elongated member 102, and therefore the radiofrequency perforation apparatus 100, may be curved or bent, as shown in FIGS. 3A-3C. As used herein, the terms 'curved' or 'bent' refer to any region of non-linearity, or any deviation from a longitudinal axis of the device, regardless of the angle or length of the curve or bend. The radiofrequency perforation apparatus 100 includes a substantially rectilinear section 302 and a curved section 300 extending from the substantially rectilinear section 302. Typically, the curved section 300 is located in the distal region 202 of the elongated member 102, and may occur over various lengths and at various angles. For example, curved section 300 may have a relatively large radius, for example between about 10 cm and about 25 cm, and may traverse a small portion of a circumference of a circle, for example between about 20 and about 40 degrees, as shown in FIG. 3B. Alternatively, the curved section 300 may have a relatively small radius, for example between about 4 cm and about 7 cm, and may traverse a substantially large portion of a circumference of a circle, for example between about 50 and about 110 degrees, as shown in FIG. 3C. In one specific embodiment, the curved section 300 begins about 8.5 cm from the distal end 206 of the elongated member 102, has a radius of about 6 cm, and traverses about 80° of a circumference of a circle. In an alternative embodiment, the curved section has a radius of about 5.4 cm and traverses about 50° of a circumference of a circle and, in a further embodiment, the curved section has a radius of about 5.7 cm and traverses about 86° of a circumference of a circle. This configuration helps in positioning the elongated member 102 such that the 206 is substantially perpendicular to the tissue through which the channel is to be created, which transmits the most energy through the elongated member 102 upon a force being exerted thereonto, giving enhanced feedback to the intended user.

The curved section 300 may be applied to the elongated member 102 by a variety of methods. For example, in one embodiment, the elongated member 102 is manufactured in a curved mold. In another embodiment, the elongated member 102 may be manufactured in a substantially straight shape, and may be placed in a heated mold to force the elongated member 102 to adopt a curved shape. Alternatively, the elongated member 102 is manufactured in a substantially straight shape may be forcibly bent by gripping the elongated member 102 just proximal to the region to be curved and applying force to curve the distal region 202. In an alternative embodiment, the elongated member 102 includes a tubular member 210 and an end member 212, as described with respect to FIG. 2D, which are joined together at an angle (not shown in the drawings). That is, rather than being coaxial, the tubular member 210 and an end member 212 may be joined such that, for example, they are at an angle of 45° with respect to each other.

As mentioned hereinabove, the proximal region 200 of the elongated member 102 may be structured to be coupled to a source of energy. For example, the proximal region 200 may comprise a hub 108, to which an energy source may be connected, and which allows for the energy source to be electrically connected to the elongated member 102. Further details regarding the hub 108 are described hereinbelow. In other embodiments, the proximal region 200 is coupled to a source of energy by other methods known to those of skill in the art, and the invention is not limited in this regard.

The elongated member 102 may be made from an electrically conductive material that is biocompatible. As used herein, 'biocompatible' refers to a material that is suitable for use within the body during the course of a surgical procedure. Such materials include stainless steels, copper, titanium and nickel-titanium alloys (for example, NITINOL®), amongst others. Furthermore, in some embodiments, different regions of the elongated member 102 may be made from different materials. In an example of the embodiment of FIG. 2D, the tubular member 210 is made from stainless steel, such that it may provide column strength to a portion of the elongated member 102, for example to the force transmitting portion, and the end member 212 is made out of a nickel-titanium alloy, such as NITINOL®, such that it may provide flexibility to a portion of the elongated member 102, for example the distal portion. Embodiments wherein the force transmitting portion of the elongated member 102 is manufactured from stainless steel, for example, may result in radiofrequency perforation apparatus 100 having a similar amount of column strength to a device of the prior art, for example a mechanical perforator such as a Brockenbrough™ needle. This may be beneficial in that it may provide a familiar 'feel' to users who have used such devices in the past. In some embodiments comprising a curved or bent elongated member 102, the rectilinear section 302 is made from stainless steel, such that it may provide column strength to the elongated member 102, and the curved section 300 is made out of a nickel-titanium alloy, such as NITINOL®, such that it may provide flexibility to the elongated member 102. In addition, the use of NITINOL® for curved section 300 is advantageous as the super-elastic properties of this material helps in restoring the shape of the curved section 300 after the curved section 300 is straightened out, for example when placed within a dilator.

As mentioned hereinabove, the elongated member 102 has an electrical insulator 104 disposed on at least a portion of the outer surface thereof. In some embodiments, for example as shown in FIG. 1A, electrical insulator 104 may cover the circumference of the elongated member 102 from the proximal region 200 of the elongated member 102 to the distal region 202 of the elongated member 102. In other words, the force transmitting portion 114 and distal portion 112 are electrically conductive and the electrical insulator substantially covers the force transmitting portion 114 and distal portion 112 with the electrode 106 substantially deprived from the electrical insulator 104. When a source of energy is coupled to the proximal region 200 of the elongated member 102, the electrical insulator 104 substantially prevents leakage of energy along the length of the elongated member 102, thus allowing energy to be delivered from the proximal region 200 of the elongated member 102 to the electrode 106.

In alternate embodiments, the electrical insulator 104 does not extend between the proximal portion and distal portion of the elongated member 102. In such embodiments, the radiofrequency perforation apparatus 100 may be positioned within a dilator (generally comprising an electrically insulating material) when in use within the patient's body. Thus, it is not necessary that the electrical insulator 104 cover the entire elongated member 102, as the dilator provides sufficient electrical insulation to prevent substantial leakage of current along the length of the elongated member 102.

Figure 1B:
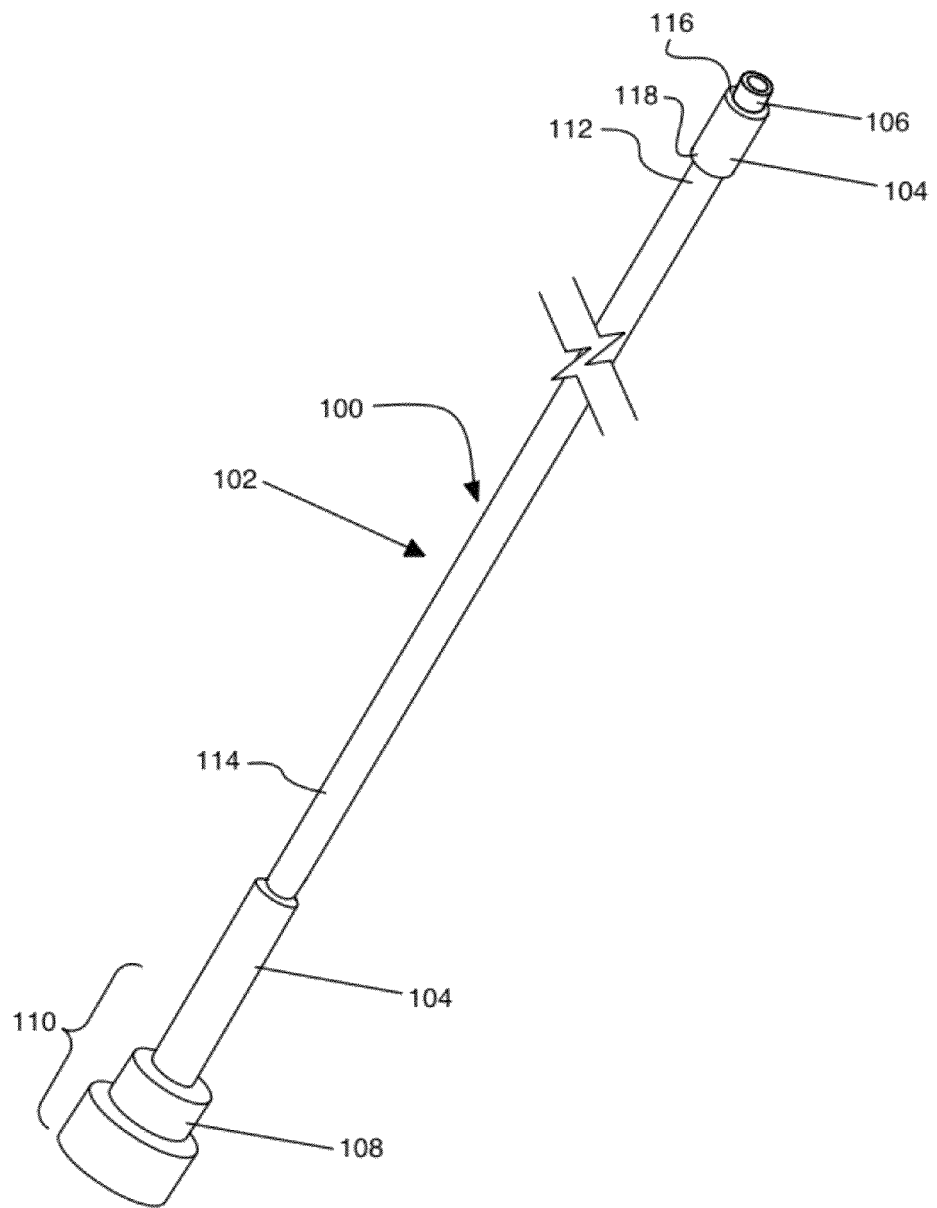
FIG. 1B, in a perspective view, illustrates a radiofrequency perforation apparatus in accordance with an alternative embodiment of the present invention.

More specifically, FIG. 1B illustrates an embodiment of the radiofrequency perforation apparatus 100 in which the electrical insulator 104 extends adjacent to the electrode 106 as well as near or into the handle 110. The insulation in and/or near the handle 110 electrically insulates the user from the electrically conductive surface of the radiofrequency perforation apparatus 100. Electrical insulator 104 is included adjacent to the electrode 106 in cases where the distal portion is advanced substantially beyond the distal end of the dilator during perforation. In such cases, it may be necessary to ensure that only a limited portion of the elongated member 102 is electrically exposed, so as to ensure that perforation may occur upon the delivery of energy, as described further herein below. In order to ensure that the surface area of the electrically exposed portion of the elongated member 102, i.e. the electrode, remains suitably small when advanced beyond the insulating dilator, electrical insulator 104 is positioned adjacent to the electrode 106. More specifically, the electrical insulator 104 extends in part substantially longitudinally along the radiofrequency perforation apparatus 100, the electrical insulator 104 defining an insulator distal end 116 located substantially adjacent to the electrode 106 and an insulator proximal end 118 located between the insulator distal end 116 and the handle 110, the insulator proximal end 118 being substantially spaced apart from the handle 110. Another portion of the electrical insulator 104 extends substantially longitudinally substantially adjacent to the handle 110 in a direction leading towards the distal portion 112 and is substantially longitudinally spaced apart from the insulator proximal end 118.

Figure 1C:
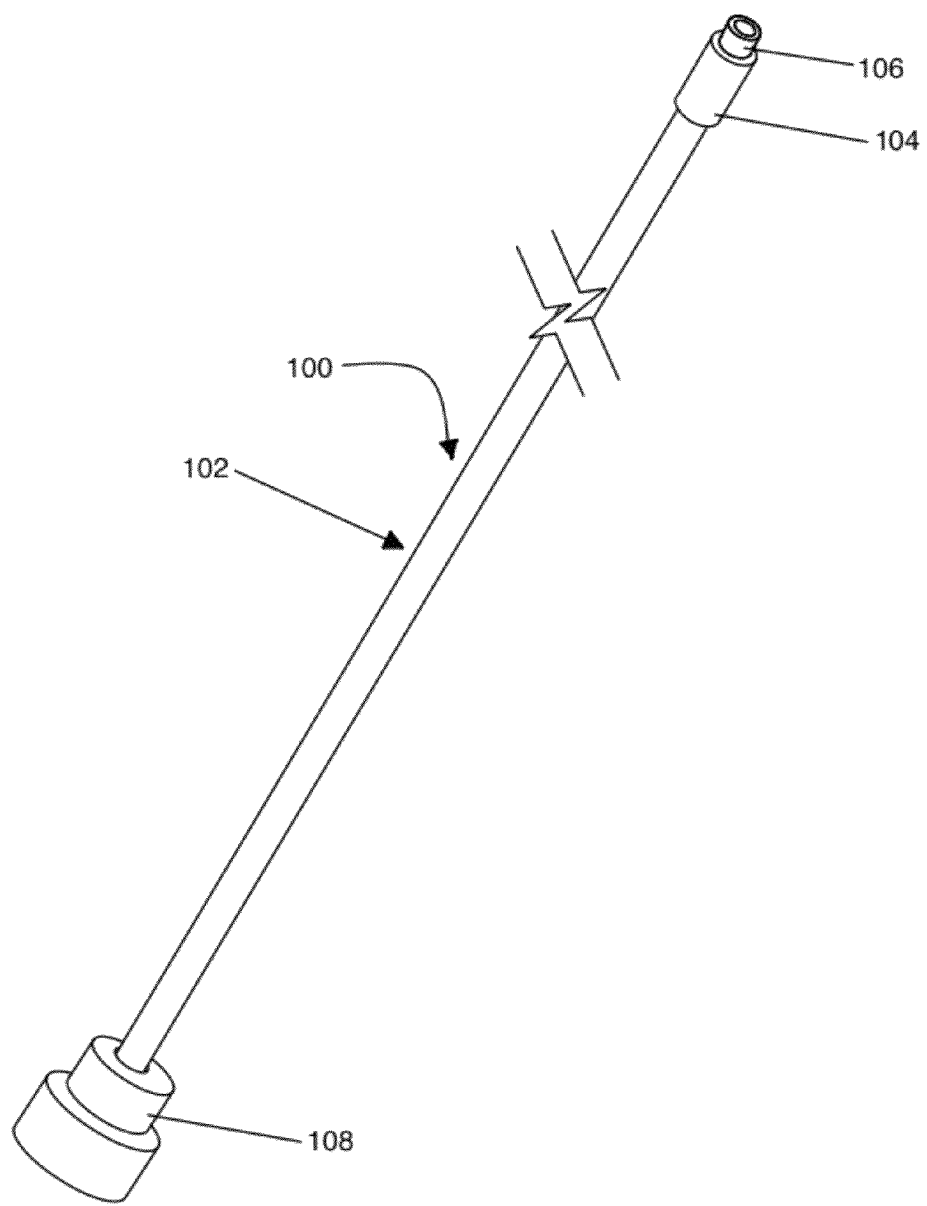
FIG. 1C, in a perspective view, illustrates a radiofrequency perforation apparatus in accordance with another alternative embodiment of the present invention.

FIG. 1C shows an alternative embodiment wherein only the area substantially adjacent the electrode 106 is insulated with the electrical insulator 104.

Figure 4A:
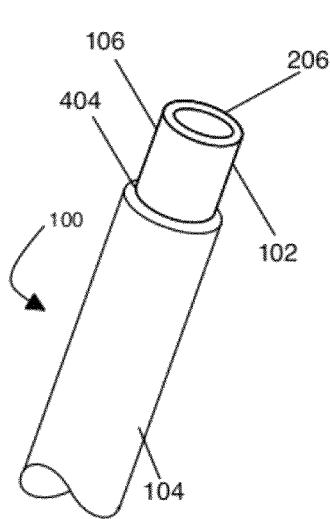
FIGS. 4A to 4H, in perspective views, illustrate various electrode configurations usable in the radiofrequency perforation apparatuses shown in FIGS. 1A to 3C.
Figure 4B:
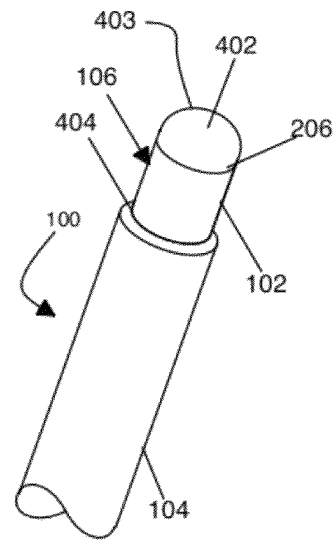
Figure 4C:
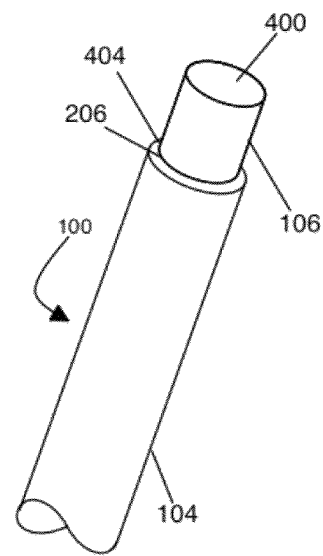
Figure 4D:
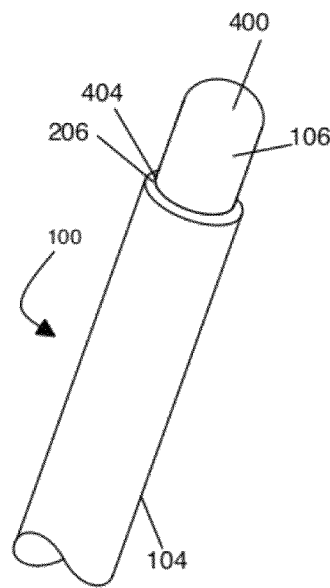
Figure 4E:
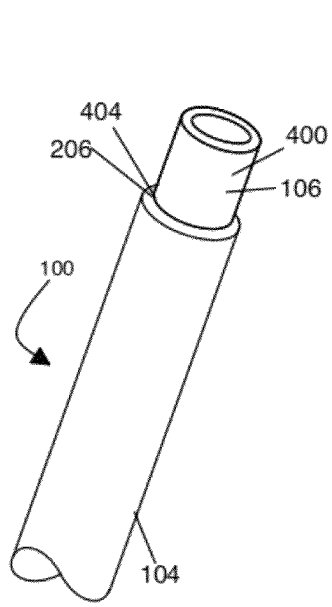
Figure 4F:
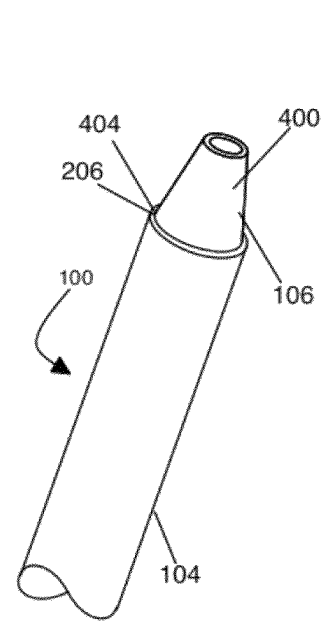

In embodiments such as illustrated in FIG. 1A, the location in the distal region 202 to which electrical insulator 104 extends may depend on the configuration of the electrode 106. Typically, electrical insulator 104 may extend to a proximal end 404 of the electrode 106, which may or may not coincide with the distal end of the elongated member 102. For example, as shown in FIGS. 4A and 4B, the distalmost 1.5 mm of the elongated member 102 may serve as at least a portion of the electrode 106. In these embodiments, electrical insulator 104 may extend to a point about 1.5 mm proximal to the distal end 206 of the elongated member 102. In the embodiments of FIGS. 4C-4D, an external component 400 coupled to the distal end of the elongated member 102 serves as the electrode 106. In such embodiments, the proximal end 404 of the electrode 106 substantially coincides with the distal end 206 of the elongated member 102, and thus the electrical insulator 104 may extend to the distal end 206 of the elongated member 102. In some embodiments, the electrical insulator 104 may extend beyond the distal end 206 of the elongated member 102, and may cover a portion of the external component 400. This may aid in securing the external component 400 to the elongated member 102. The uncovered portion of the external component 400 may then serve as the electrode 106. In other embodiments, for example as shown in FIG. 4B, the distalmost portion of the elongated member 102, as well as an external component 400, may serve as the electrode 106. In this embodiment, the electrical insulator 104 may extend to a point substantially adjacent to the distal end 206 of the elongated member 102. For example, the electrical insulator 104 may extend to a point about 1.0 mm away from the distal end 206 of the elongated member 102.

The electrical insulator 104 may be one of many biocompatible dielectric materials. Materials for electrical insulator 104 may include, but are not limited to, polytetrafluoroethylene (PTFE, Teflon®), parylene, polyimides, polyethylene terepthalate (PET), polyether block amide (PEBAX®), and polyetheretherketone (PEEK™), as well as combinations thereof. The thickness of the electrical insulator 104 may vary depending on the material used. Typically, the thickness of the electrical insulator 104 is from about 0.02 mm to about 0.12 mm.

Figure 4G:
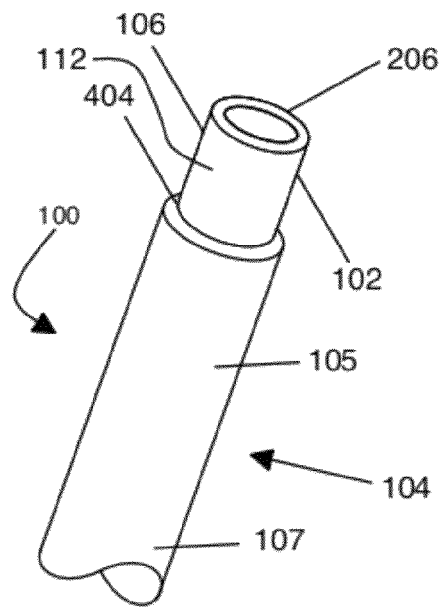

In some embodiments, the electrical insulator 104 may comprise a plurality of dielectric materials. This may be useful, for example, in cases where different properties are required for different portions of the electrical insulator 104. In certain applications, for example, substantial heat may be generated at the electrode 106. In such applications, a material with a sufficiently high melting point is required for the distalmost portion of the electrical insulator 104, so that this portion of the electrical insulator 104, located adjacent to electrode 106, doesn't melt. Furthermore, in some embodiments, a material with a high dielectric strength may be desired for all or a portion of the electrical insulator 104. In some particular embodiments, electrical insulator 104 has a combination of both of the aforementioned features. Thus, in one embodiment, as shown for example in FIG. 4G, a distalmost portion 105 of the electrical insulator 104, for example between about 1 cm and about 5 cm in length, more specifically about 2 cm to about 3 cm, comprises PTFE, which has a substantially high melting point, while the remainder 107 of the electrical insulator 104 comprises PET, which has a relatively high dielectric strength. In the embodiment shown, portions 105 and 107 abut each other; however, in other embodiments, portions 105 and 107 may at least partially overlap as shown, for example, in FIG. 6E.

With reference now to FIG. 6E, the electrical insulator 104 includes a first electrically insulating layer 218 made out of a first electrically insulating material, the first electrically insulating layer 218 substantially covering the substantially tubular member 210 substantially adjacent the end member 212 and a second electrically insulating layer 220 made out of a second electrically insulating material, the second electrically insulating layer 220 substantially covering the end member 212 with the electrode 106 substantially deprived from the second electrically insulating layer 220, said second electrically insulating 220 layer being substantially thinner than the first electrically insulating layer 218. In the illustrated embodiment, the first electrically insulating layer 218 overlaps the second electrically insulating layer 220 about the region of the taper of the elongated member 102. This configuration facilitates the obtention of desirable mechanical properties for the radiofrequency perforation apparatus 100, as thinner materials are typically less rigid than thicker materials. Also, in some embodiments of the invention, the first electrically insulating layer 218 overlaps a portion of the second electrically insulating layer 220. However, in alternative embodiments of the invention, the electrical insulator 103 has any other suitable configuration, for example, the first electrically insulating layer 218 and the second electrically insulating layer 220 being made of the same material.

Figure 4H:
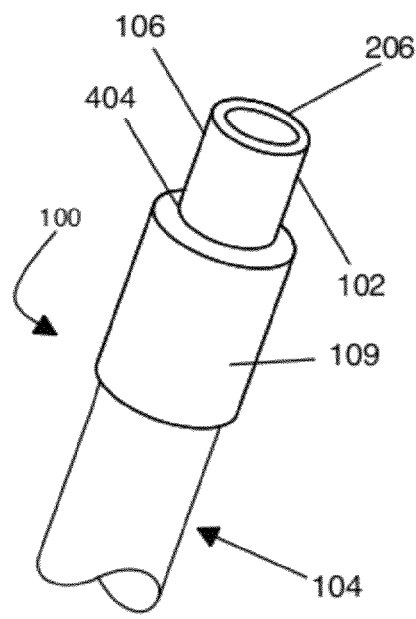

In further embodiments, for example in order to prevent a distal portion of the electrical insulator 104 from melting due to heat generated by the electrode 106, a heat shield 109 may be applied to the radiofrequency perforation apparatus 100 substantially adjacent to the electrode 106, as shown in FIG. 4H. For example, in some such embodiments, a thermally insulative material, for example Zirconium Oxide or polytetrafluoroethylene (PTFE), may be applied over approximately the distal-most 2 cm of the electrical insulator 104. Typically, the heat shield 109 protrudes substantially radially outwardly from the remainder of the distal portion 112 and substantially longitudinally from the electrode 106 in a direction leading towards the handle 110.

The electrical insulator 104 may be applied to the elongated member 102 by a variety of methods. For example, if the electrical insulator 104 includes PTFE, it may be provided in the form of heat-shrink tubing, which may be placed over the elongated member 102 and subjected to heat to substantially tighten around the elongated member 102. If the electrically insulative material is parylene, for example, it may be applied to the elongated member 102 by vapor deposition. In other embodiments, depending on the specific material used, the electrical insulator 104 may be applied to the elongated member 102 by dip-coating, co-extrusion, or spraying, for example.

As mentioned hereinabove, in embodiments of the present invention, the elongated member 102 comprises an electrode 106 at the distal region thereof, the electrode 106 configured to create a channel via radiofrequency perforation. As used herein, 'radiofrequency perforation' refers to a procedure in which radiofrequency (RF) electrical energy is applied from a device to a tissue to create a perforation or fenestration through the tissue. Without being limited to a particular theory of operation, it is believed that the RF energy serves to rapidly increase tissue temperature to the extent that water in the intracellular fluid becomes converted to steam, inducing cell lysis as a result of elevated pressure within the cell. Furthermore, electrical breakdown may occur within the cell, wherein the electric field induced by the alternating current exceeds the threshold dielectric strength of the medium located between the radiofrequency perforator and the cell, causing a dielectric breakdown. In addition, mechanical breakdown may occur, wherein alternating current induces stresses on polar molecules in the cell. Upon the occurrence of cell lysis and rupture, a void is created, allowing the device to advance into the tissue with little resistance. In order to achieve this effect, the device from which energy is applied, i.e. the electrode, is relatively small, having an electrically exposed surface area of no greater than about 15 $mm^2$, in order to increase the current density delivered to the tissue. In addition, the energy source is capable of applying a high voltage through a high impedance load, as will be discussed further hereinbelow. This is in contrast to RF ablation, whereby a larger-tipped device is utilized to deliver RF energy to a larger region in order to slowly desiccate the tissue. As opposed to RF perforation, which creates a void in the tissue through which the device may be advanced, the objective of RF ablation is to create a large, non-penetrating lesion in the tissue, in order to disrupt electrical conduction. Thus, for the purposes of the present invention, the electrode refers to a device which is electrically conductive and exposed, having an exposed surface area of no greater than about 15 mm$^2$, and which is, when coupled to a suitable energy source and positioned at a target site, operable to delivery energy to create a perforation or fenestration through tissue, for example by vaporizing intracellular fluid of cells with which it is in contact, such that a void, hole, or channel is created in the tissue located at the target site.

As mentioned hereinabove, in one embodiment, the electrode 106 may comprise the distalmost portion of the elongated member 102. That is, as shown in FIG. 4A, if the electrical insulator 104 extends from the proximal region 200 (not shown in FIG. 4A) of the elongated member 102 to a point that is substantially adjacent to the distal end 206 of the elongated member 102, the unexposed distalmost portion may serve as the electrode 106. In this embodiment, the electrode 106 may be shaped as a hollow ring or cylinder. If, for example, the outer diameter of the elongated member 102 is about 0.7 mm, the inner diameter is about 0.4 mm, and the length of the distalmost exposed portion is about 2.0 mm, then the exposed surface area of the electrode 106 will be about 4.7 mm$^2$. Having an open distal end 206, as shown in FIG. 4A, may be desirable to allow for addition and/or removal of material from a site within a patient's body. In further embodiments, as shown in FIG. 4B, it may be desirable for the distal end 206 of the elongated member 102 to be closed. For example, in some embodiments, it may be desirable for fluids to be injected radially from the elongated member 102, for example through apertures in elongated member 102 as discussed hereinbelow, substantially without being injected distally from the elongated member 102. In these embodiments, a closed distal end 206 may facilitate radial injection of fluid while preventing distal injection.

Indeed, it is a common belief that it is necessary to have a distal opening in order to properly deliver a contrast agent to a target site. However, it was found that it is nevertheless possible to properly operate the radiofrequency perforation apparatus 100 even in the absence of distal openings. Advantageously, these embodiments reduce the risk that a core of tissue becomes first stuck in such a distal opening when creating the channel through the tissue and is afterwards freed into the blood circulation, which creates risks of blocking blood vessels, leading to potentially lethal infarctions.

Thus, as shown in FIG. 4B, an external component 400, for example an electrode tip, may be operatively coupled to the distal end 206. In this embodiment, the exposed portion of the distal region 202, as well as the external component 400, serves as the electrode 106. In such an embodiment, if the outer diameter of the elongated member 102 is 0.7 mm, the external component 400 is a hemisphere having a radius of about 0.35 mm, and the length of the distalmost exposed portion of the elongated member 102 is about 2.0 mm, then the surface area of the electrode 106 is about 5.2 mm$^2$. Alternatively, as shown for example in FIG. 6E, the distal end of end member 212, rather than a separate external component, may be closed and may be used as the electrode 106.

In other embodiments, as shown for example in FIG. 4C to, an electrically conductive and exposed external component 400 is electrically coupled to the distal end of the elongated member 102, such that the external component 400 serves as the electrode 106. In such an embodiment, external component 400 may be a cylinder having a diameter of between about 0.4 mm and about 1 mm, and a length of about 2 mm. Electrode 106 thus has an exposed surface area of between about 2.6 mm$^2$ and about 7.1 mm$^2$.

The external component 400 may take a variety of shapes. For example, external component 400 may be cylindrical, tubular, conical, or truncated conical. The distal end of the external component 400 may be rounded, or flat, for example. Furthermore, the external component 400 may be made from a variety of biocompatible electrically conductive materials, for example stainless steel. The external component 400 may be coupled to the elongated member 102 by a variety of methods. In one embodiment, external component 400 may be welded to the elongated member 102. In another embodiment, external component 400 may be soldered to the elongated member 102. In one such embodiment, the solder material itself may comprise the external component 400. For example, an amount of solder may be electrically coupled to the elongated member 102 in order to function as at least a portion of the electrode 106. In further embodiments, other methods of coupling external component 400 to the elongated member 102 may be used, and the invention is not limited in this regard.

In these embodiments, as described hereinabove, the electrically exposed and conductive surface area of the electrode 106 is no greater than about 15 mm$^2$. In embodiments wherein the electrical insulator 104 covers a portion of the external component 400, the portion of the external component 400 that is covered by the electrical insulator 104 is not included when determining the surface area of the electrode 106.

Referring again to FIG. 4B, in some embodiments, the distal portion 112 defines a distal tip 403, the distal tip 403 being substantially atraumatic. In other words, the distal end of the radiofrequency perforation apparatus 100 is structured such that it is substantially atraumatic, or blunt. As used herein the terms 'atraumatic' and 'blunt' refer to a structure that is not sharp, and may include structures that are rounded, obtuse, or flat, amongst others, as shown, for example, in FIG. 4B. These embodiments, wherein the distal end of the radiofrequency perforation apparatus 100 is substantially blunt, may be beneficial in that unwanted damage to non-target areas within the body may be avoided. That is, if mechanical force is unintentionally applied to the radiofrequency perforation apparatus 100 when the distal end of the radiofrequency perforation apparatus 100 is located at a non-target tissue, the radiofrequency perforation apparatus 100 may not perforate the non-target tissue.

In some embodiments, the distal tip 403 may be substantially bullet-shaped, as shown for example in FIG. 6E, which allows the intended user to drag the distal tip 403 across the surface of tissues in the body of the patient and to catch on to tissues at the target site. For example, if the target site includes a fossa ovalis as described further hereinbelow, the bullet-shaped tip may catch on to the fossa ovalis so that longitudinal force applied at a proximal portion of apparatus 100 causes the electrode 106 to advance into and through the fossa ovalis rather than slipping out of the fossa. Because of the tactile feedback provided by the radiofrequency perforation apparatus 100, this operation facilitates positioning of the radiofrequency perforation apparatus 100 prior to energy delivery to create a channel.

As mentioned hereinabove, in some embodiments, the radiofrequency perforation apparatus 100 may comprise a hub 108 coupled to the proximal region thereof. The hub 108 may be part of the handle 110 of the radiofrequency perforation apparatus 100, may facilitate the connection of the elongated member 102 to an energy source, and may facilitate the connection of the elongated member 102 to a source of fluid, for example contrast fluid.

Figure 5:
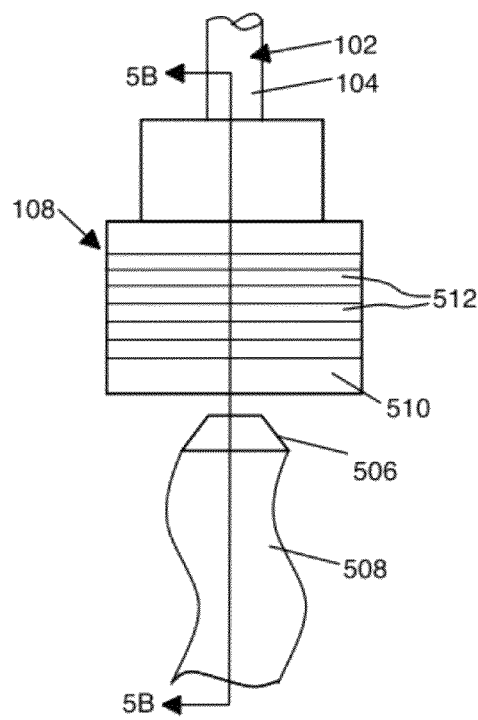
FIG. 5A, in a top elevation view, illustrates an embodiment of a hub usable in the radiofrequency perforation apparatuses shown in FIGS. 1A to 3C.
FIG. 5B, in a side cross-sectional view taken along the line 5B-5B of FIG. 5A, illustrates the hub shown in FIG. 5A.
Figure 5:
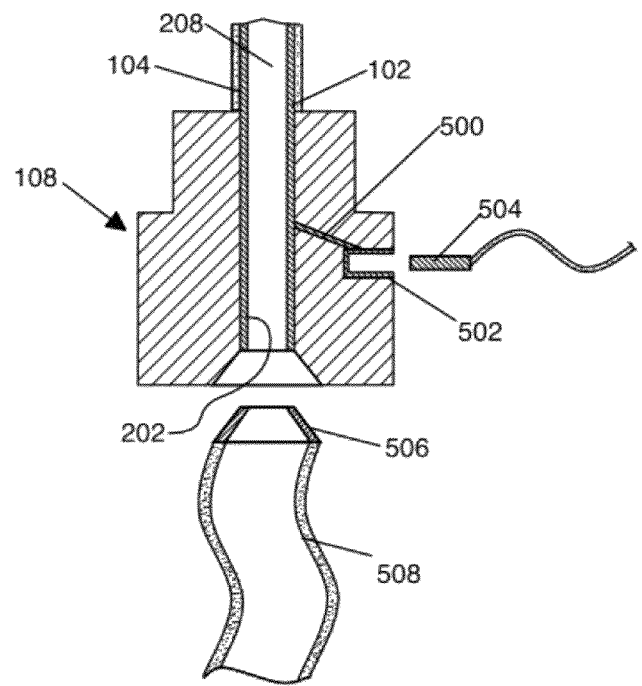

In the embodiment illustrated in FIGS. 5A-5B, the proximal region 200 the of the elongated member 102 is electrically coupled to the hub 108, which may be structured to electrically couple the elongated member 102 to a source of energy, for example a radiofrequency generator. For example, in one embodiment, the hub 108 comprises a conductive wire 500, which is connected at one end to the elongated member 102, for example by welding or brazing. The other end of the wire 500 may be coupled to a connector, for example a banana jack 502, to which a banana plug 504, electrically coupled to a source of energy, may be inserted. Thus, electrical energy may be delivered from the energy source, through plug 504, jack 502 and wire 500 to the elongated member 102 and electrode 106. In other embodiments, other hubs or connectors that may allow elongated member 102 to be connected to a source of fluid and a source of energy may be used, and the invention is not limited in this regard.

The hub 108 may further be structured to be operatively coupled to a connector 506, for example a luer lock, which may be connected to tubing 508. Tubing 508 may be structured to be operatively coupled at one end thereof to an aspirating device, a source of fluid 712, for example a syringe, or a pressure sensing device 708, for example a pressure transducer. The other end of tubing 508 may be operatively coupled the connector 506, such that tubing 508 and lumen 208 are in fluid communication with each other, thus allowing for a flow of fluid between an external device and the lumen 208.

The hub 108 may further comprise one or more curve direction or orientation indicators 510 that are located on one side of the hub 108 in order to indicate the direction of the curved section 300. The orientation indicator(s) 510 may comprise inks, etching, or other materials that enhance visualization or tactile sensation.

In some embodiments of the invention, the handle 110 includes a relatively large graspable surface so that tactile feedback can be transmitted relatively efficiently, for example by transmitting vibrations. In some embodiments of the invention, the handle 110, for example in the hub 108, includes ridges 512 that enhance this tactile feedback. Indeed, the ridges 512 allow the intended user to fully grasp the handle 110 without holding the handle 110 tightly, which facilitates the transmission of this feedback.

In some embodiments, the radiofrequency perforation apparatus 100 may define one or more apertures 600, for example as shown in FIG. 6A-6D. The one or more apertures 600 may be particularly useful in embodiments wherein a lumen 208 of the elongated member 102 is not open to the surrounding environment via the distal end of the radiofrequency perforation apparatus 100, for example in the embodiments of FIG. 4B, 4C, or 6E. In such embodiments, the lumen 208 extends substantially longitudinally through the force transmitting portion 114 and through a section of the distal portion 112 and terminates in the distal section 112 at a location substantially spaced apart from the distal tip 403, such that the distal tip 403 remains closed.

In other embodiments, the radiofrequency perforation apparatus 100 may define an open distal end 206 as well as one or more apertures 600. In embodiments comprising aperture(s) 600, the aperture(s) 600 may allow for fluids to be injected into the surrounding environment from the lumen 208, or may allow for pressure to be measured by providing a pressure transmitting lumen through radiofrequency perforation apparatus 100. For example, the aperture(s) 600 may be formed radially through elongated member 102 and electrical insulator 104, thereby allowing for fluid communication between the surrounding environment and the lumen 208. Alternatively, the aperture(s) 600 may be formed radially through a portion of the electrode 106.

The size and shape of the aperture(s) 600 may vary depending on the intended application of the radiofrequency perforation apparatus 100, and the invention is not limited in this regard. For example, in one embodiment, the aperture(s) 600 may be between about 0.25 mm and about 0.45 mm in diameter. In some embodiments, different apertures may be of different sizes. In addition, the number of apertures 600 may vary, and they may be located anywhere along the radiofrequency perforation apparatus 100 that does not interfere with the functioning of the device. For example, as shown in FIG. 6A, the radiofrequency perforation apparatus 100 includes two apertures 600 located about 1 cm from the distal end of the elongated member 102, at substantially the same longitudinal position along the elongated member 102. In another embodiment, as shown in FIG. 6B, the radiofrequency perforation apparatus 100 includes about 3 apertures located at the same circumferential position and spaced longitudinally, for example at about 1.0, 1.5, and 2.0 cm from the distal end of the elongated member 102. In another embodiment, as shown in FIG. 6C, the aperture(s) 600 are staggered, such that they are spaced apart both circumferentially as well as longitudinally. In a further embodiment, as shown in FIG. 6D, the aperture(s) 600 are located on the electrode 106. In some embodiments, the aperture(s) 600 may have a smooth or rounded wall, which may serve to minimize or reduce trauma to bodily tissue. For example, some such embodiments may comprise one or more aperture(s) 600 with a smooth outer circumferential edge created by sanding the circumferential edges to a smooth finish, or by coating the edges with a lubricious material, for example.

In some embodiments of the invention, the radiofrequency perforation apparatus 100, as shown in FIG. 6E, defines a lumen peripheral surface 602 extending substantially peripherally relatively to the lumen 216, the lumen peripheral surface 602 being substantially covered with a lumen electrically insulating material 604. This configuration prevents or reduces electrical losses from the lumen peripheral surface 602 to any electrically conducive fluid located within the lumen 208. However, in other embodiments of the invention, the lumen peripheral surface 602 is not substantially covered with the lumen electrically insulating material 604.

Also, in some embodiments of the invention including the curved section 300, the curved section 300 defines a center of curvature (not shown in the drawings) and the aperture(s) 600 extend from the lumen 208 substantially towards the center of curvature. This configuration substantially prevents the edges of the aperture(s) 600 from catching onto tissues as the tissues are perforated. However, in alternative embodiments of the invention, the aperture(s) 600 extend in any other suitable orientation.

Figure 7:
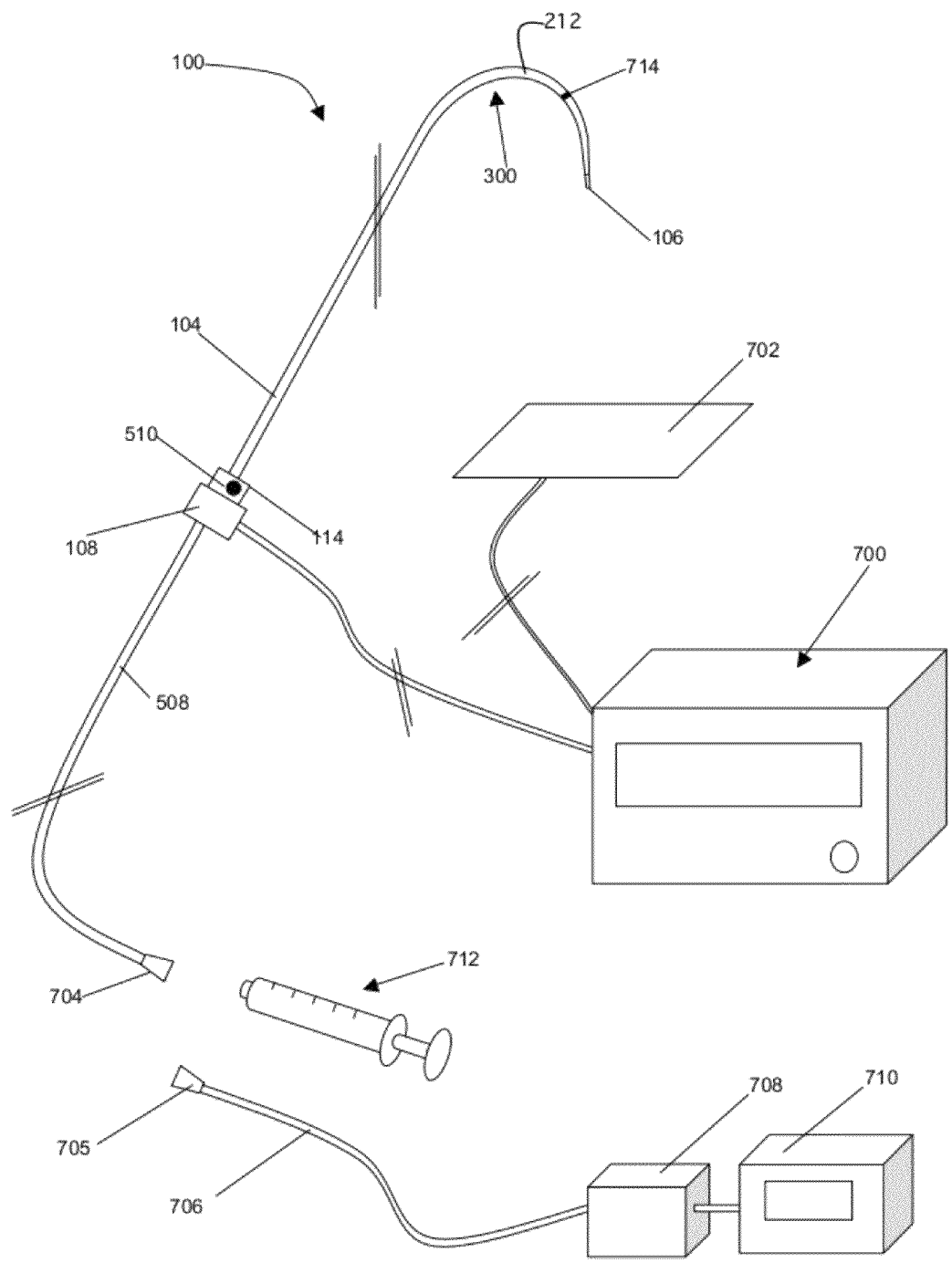
FIG. 7, in a perspective view, illustrates a system including a radiofrequency perforation apparatus in accordance with the present invention.

In some embodiments, one or more radiopaque markers 714 (as shown in FIG. 7) are associated with the radiofrequency perforation apparatus 100 to highlight the location of important landmarks on radiofrequency perforation apparatus 100. Such landmarks may include the location where the elongated member 102 begins to taper, the location of the electrode 106, or the location of any aperture(s) 600. In some embodiments, the entire distal region 202 of the radiofrequency perforation apparatus 100 may be radiopaque. This can be achieved by filling the electrical insulator 104, for example Pebax®, with a radiopaque filler, for example Bismuth.

In some embodiments, radiofrequency perforation apparatus 100 may comprise means for modifying the shape thereof. For example, in some applications, it may be desired that radiofrequency perforation apparatus 100 be capable of changing between a straight configuration, for example as shown in FIG. 1, and a curved configuration, for example as shown in FIGS. 3A-3C. This may be accomplished by coupling a pull-wire to the radiofrequency perforation apparatus 100, such that the distal end of the pull-wire is operatively coupled to the distal region of the radiofrequency perforation apparatus 100. When a user applies force to the proximal end of the pull wire, either directly or through an actuating mechanism, the distal region 202 of the radiofrequency perforation apparatus 100 is forced to deflect in a particular direction. In other embodiments, other means for modifying the shape of the radiofrequency perforation apparatus 100 may be used, and the invention is not limited in this regard.

In some embodiments, the radiofrequency perforation apparatus 100 includes at least one further electrically conductive component, located proximally relative to the electrode 106. For example, the at least one further conductive component may be a metal ring positioned on or around the insulative material 104, and may have a sufficiently large surface area so as to be operable as a return electrode. In such an embodiment, the radiofrequency perforation apparatus 100 may function in a bipolar manner, whereby electrical energy flows from the electrode 106, through tissue at the target site, to the at least one further electrically conductive component. Furthermore, in such embodiments, the radiofrequency perforation apparatus 100 includes at least one electrical conductor, for example a wire, for conducting electrical energy from the at least one further conductive component to a current sink, for example circuit ground.

Referring to FIG. 7, systems for use with the radiofrequency perforation apparatus 100 typically comprise an energy source 700 and, in some embodiments, a grounding pad 702, tubing, a pressure transducer, and/or a source of fluid 712.

Radiofrequency perforation apparatus 100 may be used in conjunction with a source of radiofrequency energy suitable for perforating material within a patient's body. The source of energy may be a radiofrequency (RF) electrical generator 700, operable in the range of about 100 kHz to about 1000 kHz, and designed to generate a high voltage over a short period of time. More specifically, in some embodiments, the voltage generated by the generator increases from about 0 V (peak-to-peak) to greater than about 75 V (peak-to-peak) in less than about 0.6 seconds. The maximum voltage generated by generator 700 may be between about 180V peak-to-peak and about 3000V peak-to-peak. The waveform generated may vary, and may include, for example, a sine-wave, a rectangular-wave, or a pulsed rectangular wave, amongst others. During delivery of radiofrequency energy, the impedance load may increase due to tissue lesioning near the target-site, or the formation of a vapor layer following cell rupture, for example. The generator 700 may be operable to continue to increase the voltage, even as the impedance load increases. For example, energy may be delivered to a tissue within a body at a voltage that rapidly increases from about 0 V (RMS) to about 220 V (RMS) for a period of between about 0.5 seconds and about 5 seconds.

Without being limited to a particular theory of operation, it is believed that under particular circumstances, as mentioned hereinabove, dielectric breakdown and arcing may occur upon the delivery of radiofrequency energy, whereby polar molecules may be pulled apart. The combination of these factors may result in the creation of an insulative vapor layer around the electrode, therein resulting in an increase in impedance, for example the impedance may increase to greater than 4000Ω. In some embodiments, despite this high impedance, the voltage continues to increase. Further increasing the voltage increases the intensity of fulguration, which may be desirable as it allows for an increased perforation rate. An example of an appropriate generator for this application is the BMC RF Perforation Generator (model number RFP-100, Baylis Medical Company, Montreal, Canada). This generator delivers continuous RF energy at about 460 kHz.

A grounding pad or dispersive electrode 702 may be electrically coupled to the generator 700 for contacting or attaching to the body of the patient to provide a return path for the RF energy when the generator 700 is operated in a monopolar mode. Alternatively, in embodiments utilizing a bipolar device, for example as described hereinabove, a grounding pad may not be necessary as a return path for the RF energy may be provided by the further conductive component.

In the embodiment illustrated in FIGS. 5A, 5B and 7, the radiofrequency perforation apparatus 100 is operatively coupled to the tubing 508 using connector 506 located at the proximal end of the radiofrequency perforation apparatus 100. In some embodiments, the tubing 508 is made of a polymeric material, for example polyvinylchloride (PVC), or another flexible polymer. The tubing 508 may further be operatively coupled to an adapter 704, which may be structured to provide a flexible region for the user to the handle when releaseably coupling an external pressure transducer, a fluid source or other devices to the adapter. Couplings between elongated member 102, connector 506, and tubing 508, and between tubing 508 and adapter 704, may be temporary, for example using Luer locks or other releasable components, or may be substantially permanent, for example using an adhesive such as a UV curable adhesive, an epoxy, or another type of bonding agent.

Referring to FIG. 7, as mentioned hereinabove, in order to measure pressure at the distal region 202 of the radiofrequency perforation apparatus 100, an external pressure transducer may be coupled to the radiofrequency perforation apparatus 100. For example, an adapter 705 may be operatively coupled to the external tubing 706, which may be operatively coupled to an external pressure transducer 708. The adapter 705 may be structured to facilitate coupling to adapter 704 when in use. For example, adapters 704 and 705 may comprise male and female Luer locks or other connectors, adapted to readily couple and decouple to/from each other. In use, tubing 706 and 508 may be flushed with saline or another suitable fluid to remove air bubbles prior to measuring pressure. When radiofrequency perforation apparatus 100 is positioned in a vessel, conduit or cavity of a body, fluid adjacent the distal region 202 exerts pressure through the aperture(s) 600 and/or open distal end 206 on fluid within the lumen 208, which in turn exerts pressure on fluid in tubing 508 and 706, which further exerts pressure on external pressure transducer 708. The aperture(s) 600 and the lumen 208 thus provide a pressure sensor in the form of a pressure transmitting lumen for coupling to a pressure transducer.

The external pressure transducer 708 produces a signal that varies as a function of the pressure it senses. The external pressure transducer 708 is electrically coupled to a pressure monitoring system 710 that is operative to convert the signal provided by the transducer 708 and display a pressure contour as a function of time, for example. Thus, pressure may be optionally measured and/or recorded and, in accordance with one embodiment of a method aspect as described further herein below, used to determine a position of the distal region 202. In those embodiments of the radiofrequency perforation apparatus 100 that do not comprise a lumen in fluid communication with the outside environment, a pressure transducer may be mounted at or proximate to the distal portion 112 of the radiofrequency perforation apparatus 100 and coupled to a pressure monitoring system, for example via an electrical connection.

As previously mentioned, the radiofrequency perforation apparatus 100 may be operatively coupled to a source of fluid 712 for delivering various fluids to the radiofrequency perforation apparatus 100. The source of fluid 712 may be, for example, an IV bag or a syringe. The source of fluid 712 may be operatively coupled to the lumen 208 via the tubing 508 and the adapter 704, as mentioned hereinabove. Alternatively, or in addition, the radiofrequency perforation apparatus 100 may be operatively coupled to an aspiration device for removing material from the patient's body through open distal end 206 and/or one or more of the apertures 600.

In one broad aspect, the electrosurgical radiofrequency perforation apparatus 100 is usable to deliver energy to a target site within a body of a human or animal to perforate or create a void or channel in a material at the target site. Further details regarding delivery of energy to a target site within the body may be found in U.S. patent application Ser. Nos. 10/347,366 (filed on Jan. 21, 2003), Ser. No. 10/760,749 (filed on Jan. 21, 2004), Ser. No. 10/666,288 (filed on Sep. 19, 2003), and Ser. No. 11/265,304 (filed on Nov. 3, 2005), and U.S. Pat. No. 7,048,733 (application Ser. No. 10/666,301, filed on Sep. 19, 2003) and U.S. Pat. No. 6,565,562 (issued on May 20, 2003), all of which are incorporated herein by reference.

In one specific embodiment, the target site may comprise a tissue within the heart of a patient, for example the atrial septum of the heart. In such an embodiment, the target site may be accessed via the inferior vena cava (IVC), for example through the femoral vein.

In one such embodiment, an intended user introduces a guidewire into a femoral vein, typically the right femoral vein, and advances it towards the heart. A guiding sheath, for example a sheath as described in U.S. patent application Ser. No. 10/666,288 (filed on Sep. 19, 2003), previously incorporated herein by reference, is then introduced into the femoral vein over the guidewire, and advanced towards the heart. The distal ends of the guidewire and sheath are then positioned in the superior vena cava. These steps may be performed with the aid of fluoroscopic imaging. When the sheath is in position, a dilator, for example the TorFlex™ Transseptal Dilator of Baylis Medical Company Inc. (Montreal, Canada), or the dilator as described in U.S. patent application Ser. No. 11/727,382 (filed on Mar. 26, 2007), incorporated herein by reference, is introduced into the sheath and over the guidewire, and advanced through the sheath into the superior vena cava. The sheath may aid in preventing the dilator from damaging or puncturing vessel walls, for example in embodiments comprising a substantially stiff dilator. Alternatively, the dilator may be fully inserted into the sheath prior to entering the body, and both may be advanced simultaneously towards the heart. When the guidewire, sheath, and dilator have been positioned in the superior vena cava, the guidewire is removed from the body, and the sheath and dilator are retracted slightly, such that they enter the right atrium of the heart. An electrosurgical device, for example radiofrequency perforation apparatus 100 described hereinabove, is then introduced into the lumen of the dilator, and advanced toward the heart.

In this embodiment, after inserting the electrosurgical device into the dilator, the user may position the distal end of the dilator against the atrial septum. The electrosurgical device is then positioned such that electrode 106 is aligned with or protruding slightly from the distal end of the dilator. When the electrosurgical device and the dilator have been properly positioned, for example against the fossa ovalis of the atrial septum, a variety of additional steps may be performed, such as measuring one or more properties of the target site, for example an electrogram or ECG (electrocardiogram) tracing and/or a pressure measurement, or delivering material to the target site, for example delivering a contrast agent through aperture(s) 600 and/or open distal end 206. Such steps may facilitate the localization of the electrode 106 at the desired target site. In addition, as mentioned hereinabove, the tactile feedback provided by the proposed radiofrequency perforation apparatus 100 is usable to facilitate positioning of the electrode 106 at the desired target site.

With the electrosurgical device and the dilator positioned at the target site, energy is delivered from the energy source, through radiofrequency perforation apparatus 100, to the target site. For example, if the radiofrequency perforation apparatus 100 is used, energy is delivered through the elongated member 102, to the electrode 106, and into the tissue at the target site. In some embodiments, the energy is delivered at a power of at least about 5 W at a voltage of at least about 75 V (peak-to-peak), and, as described hereinabove, functions to vaporize cells in the vicinity of the electrode, thereby creating a void or perforation through the tissue at the target site. If the heart was approached via the inferior vena cava, as described hereinabove, the user applies force in the substantially cranial direction to the handle 110 of the electrosurgical device as energy is being delivered. The force is then transmitted from the handle to the distal portion 112 of the radiofrequency perforation apparatus 100, such that the distal portion 112 advances at least partially through the perforation. In these embodiments, when the distal portion 112 has passed through the target tissue, that is, when it has reached the left atrium, energy delivery is stopped. In some embodiments, the step of delivering energy occurs over a period of between about 1 s and about 5 s.

At this point in the procedure, the diameter of the perforation is typically substantially similar to the outer diameter of the distal portion 112. In some embodiments, the user may wish to enlarge the perforation, such that other devices, for example ablation catheters or other surgical devices, may pass therethrough. To do this, the user may apply force to the proximal region of the dilator. The force may, for example, be applied in the cranial direction if the heart was approached via the inferior vena cava. The force may cause the distal end of the dilator to enter the perforation, and pass through the atrial septum. The electrosurgical device may aid in guiding the dilator through the perforation, in that it may act as a substantially stiff rail for the dilator. In such embodiments, a curve, for example curved section 300 of the radiofrequency perforation apparatus 100, may assist in anchoring the electrosurgical device in the left atrium. As force is applied, portions of the dilator of larger diameter may pass through the perforation, thereby dilating, expanding, or enlarging the perforation. In some embodiments, the user may also apply torque to aid in maneuvering the dilator. Alternatively, in embodiments wherein the device is tapered, for example as described hereinabove, the device may be advanced further into the left atrium, such that larger portions of the device may enter and dilate the perforation.

When the perforation has been dilated to a suitable size, the user may stop advancing the dilator. The guiding sheath may then be advanced over the dilator through the perforation. Alternatively, the sheath may be advanced simultaneously with the dilator. At this point in the procedure, the user may retract the dilator and the electrosurgical device proximally through the sheath, leaving only the sheath in place in the heart. The user may then perform a surgical procedure on the left side of the heart, via the sheath. For example, the user may introduce a surgical device into the femoral vein through the sheath, and perform a surgical procedure to treat electrical or morphological abnormalities within the left side of the heart.

If an apparatus of the present invention, as described hereinabove, is used to carry out a procedure as described herein, then the user may maintain the 'feel' of a mechanical perforator, for example a Brockenbrough™ needle, without requiring a sharp tip and large amounts of mechanical force to perforate the atrial septum. Rather, a radiofrequency perforator, for example the electrode 106, is used to create a void or channel through the atrial septum, as described hereinabove, while reducing the risk of accidental puncture of non-target tissues.

In other embodiments, methods of the present invention may be used for treatment procedures involving other regions within the body, and the invention is not limited in this regard. For example, rather than the atrial septum, embodiments of devices, systems and methods of the present invention may be used to treat pulmonary atresia. In some such embodiments, a sheath is introduced into the vascular system of a patient, and guided to the heart, as described hereinabove. A dilator is then introduced into the sheath, and advanced towards the heart, where it is positioned against the pulmonary valve. An electrosurgical device comprising an electrode is then introduced into the proximal region of the dilator, and guided therethrough, such that it is also positioned against the pulmonary valve. Energy is then delivered from the energy source, through the electrode of the electrosurgical device, to the pulmonary valve, such that a perforation or void is created therethrough, as described hereinabove. When the electrosurgical device has passed through the valve, the user may apply a force, for example in a substantially cranial direction, to the proximal region of the dilator. The force may be transmitted to the distal region of the dilator, such that the distal region of the dilator enters the perforation and advances through the pulmonary valve. As regions of the dilator of larger diameter pass through the perforation, the perforation or channel becomes dilated.

In other applications, embodiments of a device of the present invention may be used to create voids or channels within or through other tissues of the body, for example within or through the myocardium of the heart. In other embodiments, the device may be used to create a channel through a fully or partially occluded lumen within the body. Examples of such lumens may include, but are not limited to, blood vessels, the bile duct, airways of the respiratory tract and vessels and/or tubes of the digestive system, the urinary tract and/or the reproductive system. In such embodiments, the device may be positioned such that an electrode of the device is substantially adjacent the material to be perforated. Energy may be delivered from an energy source, through the electrode 106, to the target site such that a void, perforation, or channel is created in or through the tissue.

A device having substantially similar physical and/or mechanical properties as prior art mechanical perforation devices, while being structured to allow for operation as a radiofrequency perforating device, provides benefits not found in either type of perforating device individually. More specifically, such a device maintains the 'feel' that users of such mechanical devices have become accustomed to, while providing safer and more efficient radiofrequency perforation technology for use in treatment procedures.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

What is claimed is:

1. A radiofrequency perforation apparatus for creating a channel at a target location in a body of a patient, said radiofrequency perforation apparatus comprising:
   an electrically conductive substantially tubular member defining a tubular member lumen;
      an end member partially positioned within said tubular member lumen at a distal end of said tubular member, said end member being electrically coupled to said tubular member to receive electrical energy therefrom, said end member including an electrode, wherein said end member extends distally relative to said distal end of said tubular member; and
      an electrical insulator extending along said substantially tubular member.

2. A radiofrequency perforation apparatus as defined in claim 1, wherein said electrical insulator includes a first electrically insulating layer at least partially covering said substantially tubular member and a second electrically insulating layer at least partially covering said end member, said second electrically insulating layer being thinner than said first electrically insulating layer.

3. A radiofrequency perforation apparatus as defined in claim 1, wherein said electrode is substantially atraumatic.

4. A radiofrequency perforation apparatus as defined in claim 1, wherein said electrical insulator extends along at least a portion of said end member with said electrode substantially deprived from said electrical insulator.

5. A radiofrequency perforation apparatus as defined in claim 4, wherein said end member further defines an end member lumen, said end member lumen being in fluid communication with said tubular member lumen, and wherein said end member and said electrical insulator define an aperture extending substantially radially outwardly from said end member lumen through said electrical insulator.

6. A radiofrequency perforation apparatus as defined in claim 1, wherein said radiofrequency perforation apparatus comprises a distal tip having a substantially bullet-shaped configuration.

7. A radiofrequency perforation apparatus as defined in claim 1, wherein said electrode is mechanically coupled to a portion of said end member external to said tubular member lumen.

8. A radiofrequency perforation apparatus as defined in claim 1, wherein said electrode is integral with said end member.

9. A radiofrequency perforation apparatus as defined in claim 1, wherein said substantially tubular member and said end member are coupled to each other using a method selected from the group consisting of welding, soldering, friction fitting, and using adhesives.

10. A radiofrequency perforation apparatus as defined in claim 1, wherein a total length of said substantially tubular member and said end member partially positioned therein is from about 30 cm to about 100 cm.

11. A radiofrequency perforation apparatus as defined in claim 1, wherein said substantially tubular member has a tubular member length of about 50 cm to about 100 cm and said end member has an end member length of about 2.5 cm to about 10 cm.

12. A radiofrequency perforation apparatus as defined in claim 1, wherein said substantially tubular member has a tubular member outer diameter of about 1.15 mm to about 1.35 mm and said end member has an end member outer diameter of about 0.40 mm to about 0.80 mm.

13. A radiofrequency perforation apparatus as defined in claim 1, wherein said substantially tubular member is made out of stainless steel.

14. A radiofrequency perforation apparatus as defined in claim 1, wherein said end member is made out of a nickel-titanium alloy.

15. A radiofrequency perforation apparatus as defined in claim 1, wherein said end member further defines an end member lumen, a tubular member lumen diameter of said tubular member lumen and an end member lumen diameter of said end member lumen being substantially similar for reducing turbulence in fluids flowing through said tubular member lumen and said end member lumen.

16. A radiofrequency perforation apparatus as defined in claim 1, wherein said end member further defines an end member lumen, said end member lumen being in fluid communication with said tubular member lumen, and wherein said end member defines a closed distal end.

17. A radiofrequency perforation apparatus as defined in claim 1, wherein said radiofrequency perforation apparatus includes a substantially rectilinear section and a curved section extending from said substantially rectilinear section.

18. A radiofrequency perforation apparatus as defined in claim 17, wherein said substantially rectilinear section is made out of a stainless steel and wherein said curved section is made out of nickel-titanium alloy.

19. A radiofrequency perforation apparatus as defined in claim 1, wherein said end member further defines an end member lumen, said end member lumen being in fluid communication with said tubular member lumen, and wherein said end member defines an aperture extending substantially radially outwardly from said end member lumen.

20. A radiofrequency perforation apparatus as defined in claim 19, wherein at least a portion of said tubular member and said end member together define a curved section defining a center of curvature, said aperture extending from said end member lumen substantially towards said center of curvature.

21. A radiofrequency perforation apparatus as defined in claim 19, wherein said end member defines an end member inner surface, said end member inner surface being substantially covered with an inner surface electrically insulating material.

\* \* \* \* \*